United States Patent [19]

McGrew

[11] Patent Number: 4,601,723
[45] Date of Patent: Jul. 22, 1986

[54] TELESCOPING SELF-ADJUSTING OSSICULAR PROSTHESES

[76] Inventor: Robert N. McGrew, 14910 Cantrell, Little Rock, Ark. 72212

[21] Appl. No.: 695,835

[22] Filed: Jan. 29, 1985

[51] Int. Cl.$^4$ .............................................. A61F 2/18
[52] U.S. Cl. ..................... 623/10; 128/92 C
[58] Field of Search .............. 403/104, 109, 70; 604/264; 128/334 R, 334 C, 1 R, 92 C; 3/1, 1.9

[56] References Cited

U.S. PATENT DOCUMENTS

| | | | |
|---|---|---|---|
| 963,346 | 7/1910 | Wilt | 403/109 |
| 3,254,651 | 6/1966 | Collito | 128/334 C |
| 3,710,399 | 1/1973 | Hurst | 3/1.9 |
| 4,281,419 | 8/1981 | Treace | 128/92 C |
| 4,326,512 | 4/1982 | Peerless | 128/151 |

Primary Examiner—Richard J. Apley
Assistant Examiner—David J. Isabella
Attorney, Agent, or Firm—Stephen D. Carver

[57] ABSTRACT

Ossicular prostheses for total reconstructive surgery of an infection-destroyed or traumatically damaged middle ear. Each prosthesis comprises a pair of cooperating assemblies which are adapted to be extended between the tympanic membrane and the fenestra vestibuli (oval window) in replacement of the auditory ossicles, namely the malleus, incus, and stapes. In the best mode a first rigid, preferably stainless steel shaft is pivotally received by a flanged socket surgically secured to the ear drum. Flanged socket structure secured surgically to the oval window receives the balled end of an outwardly projecting, rigid, generally tubular shaft. The extreme end of the latter shaft is adapted to be axially mated with the first shaft which is coaxially, slidably telescoped thereto. In an alternative embodiment each of the two cooperating assemblies preferably comprises elongated shaft structure including twin, parallel, closely-spaced shaft members which originate from an integral loop-like base. The base portion of the first assembly is adapted to be sutured to at least a portion of the reconstructed tympanic membrane, and the base portion of the other shaft assembly is adapted to be secured with fascia in contact with the oval window. The elongated shafts are coupled together permitting length compensating, relative axial displacements. An extensible bridge is thus established in replacement of the middle ear ossicles by the installed prosthesis and variations in air pressure etc., experienced by the thus-repaired human ear are compensated for by pivotal and/or swivelling movement of the prosthesis and by relative axial displacements facilitated by the coupled shaft assemblies thereof.

6 Claims, 17 Drawing Figures

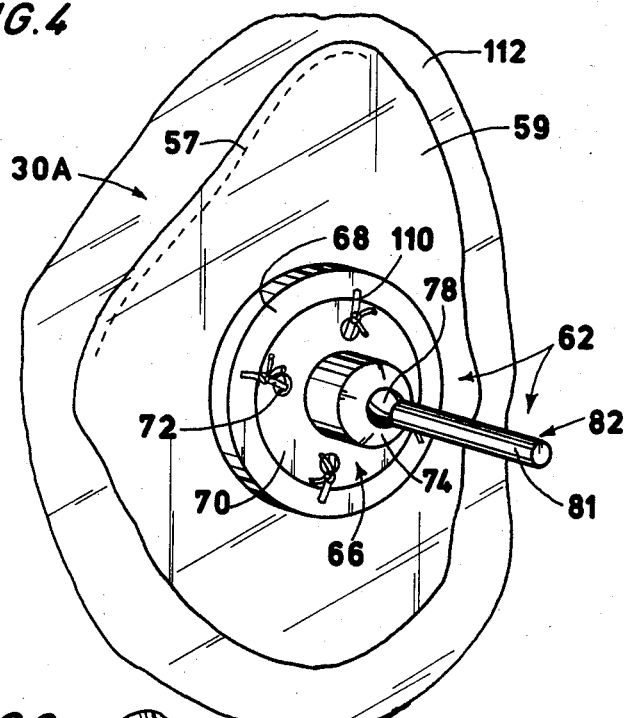
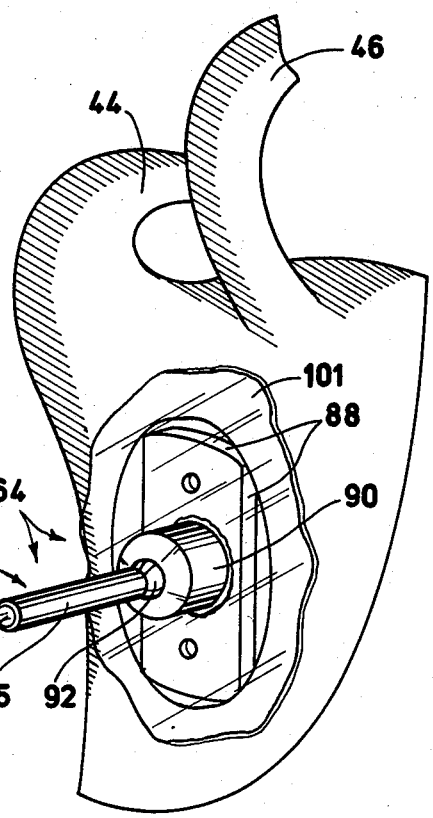
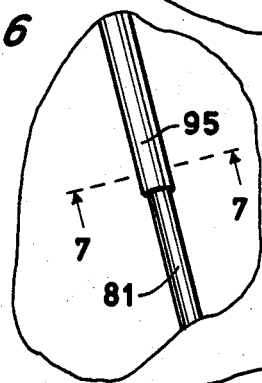
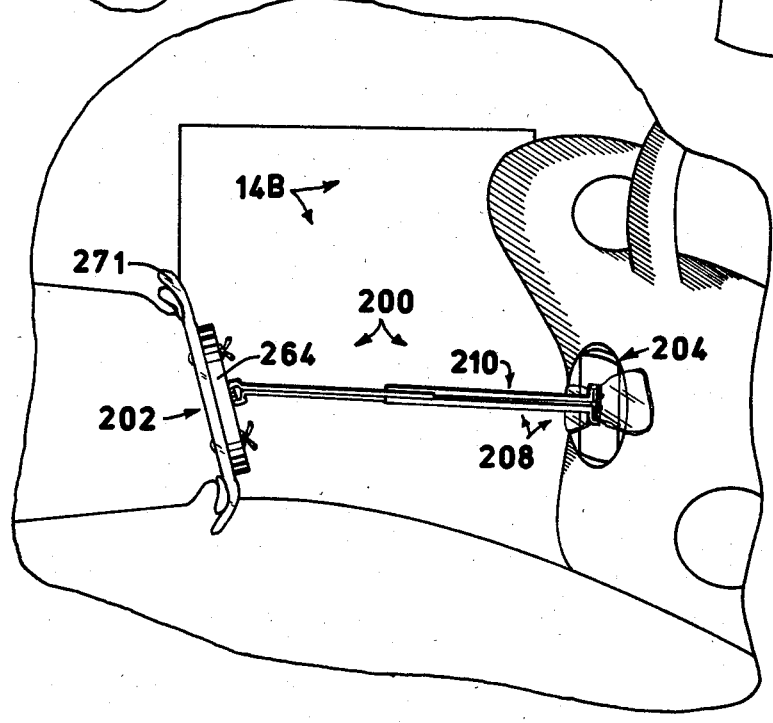

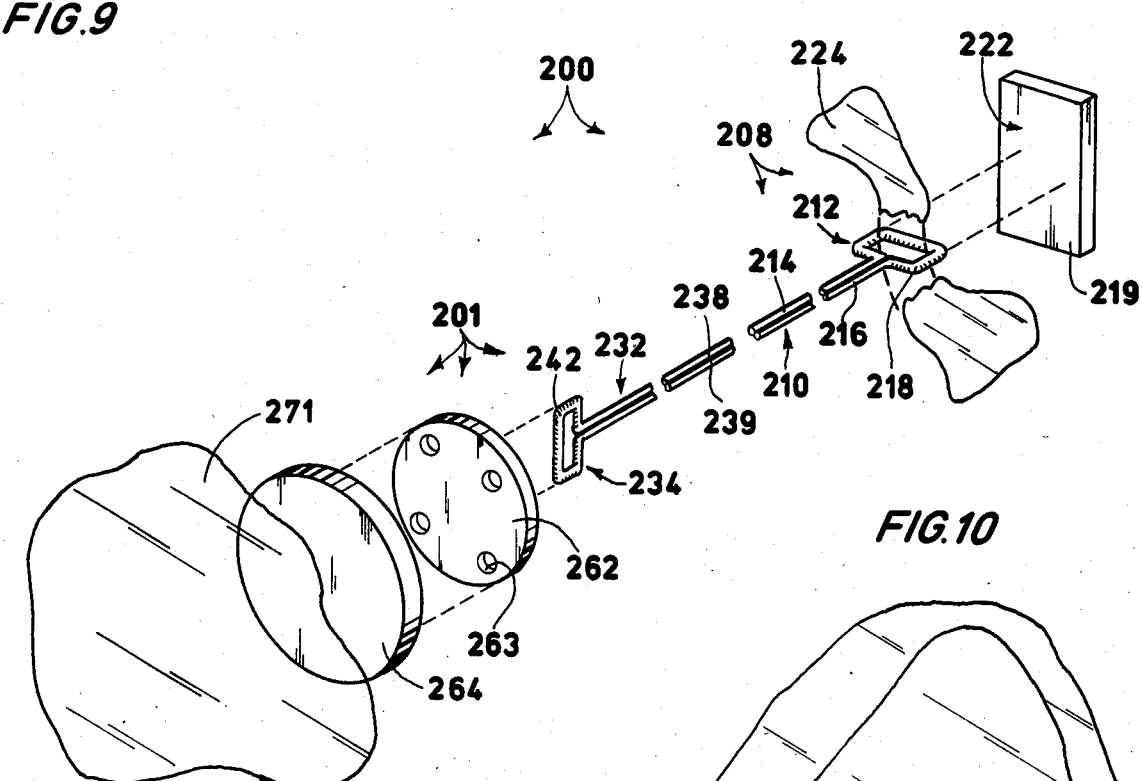
FIG.9
FIG.10
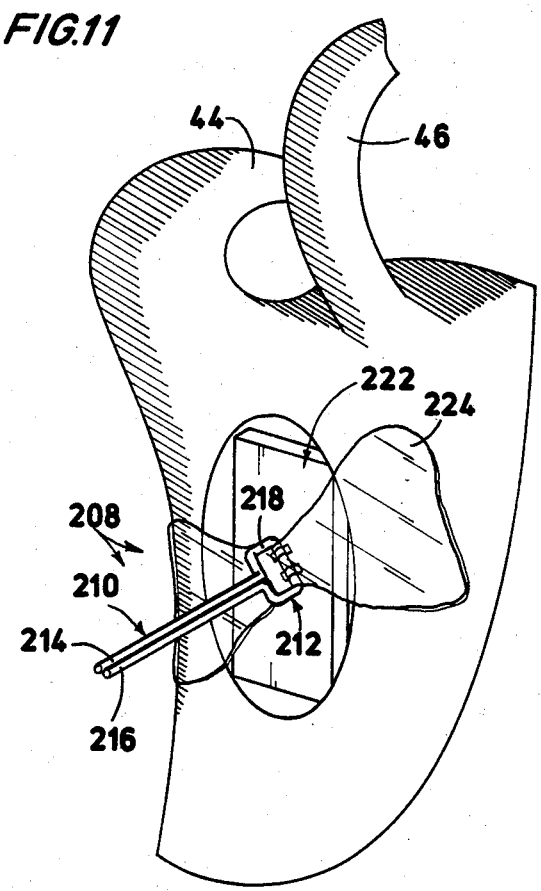
FIG.11
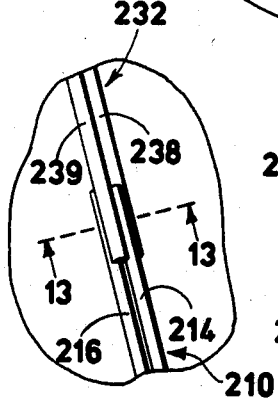
FIG.12
FIG.13

TELESCOPING SELF-ADJUSTING OSSICULAR PROSTHESES

BACKGROUND OF THE INVENTION

The present invention relates generally to prosthetic devices for middle ear reconstructive surgery. More particularly, the present invention is directed to ossicular prosthetic devices for replacement of the middle ear auditory ossicles.

The human ear is an extremely complex and intricate organ which, through a variety of processes, not all of which are presently understood, provides the valuable sense of hearing. As will be well appreciated by those skilled in the art, the structure of the human ear is typically divided into external, middle, and inner ear portions. The external ear comprises that portion which encompasses the auricle as well as the auditory or ear canal which terminates in the tympanic membrane or ear drum. The middle ear is concerned primarily with the transformation of acoustic energy into mechanical energy, whereas the inner ear is concerned with the transduction of mechanical energy into neural impulses. The middle ear is a rather irregular air filled space in the petrous portion of the temporal bone. The three small bones, or ossicles of the middle ear are the malleus, the incus, and the stapes, which provide mechanical linkage between the tympanic membrane and the fenestra vestibuli. The fenestra vestibuli is an opening in the vestibule of the inner ear and it is commonly referred to as the oval window. The malleus includes a handle which is normally attached to the tympanic membrane, and the stapes includes a footplate which is normally secured in the oval window membrane.

Middle ear air pressure is equalized by the eustachian tube which connects the middle ear and the nasopharynx. This pressure equalization is necessary for normal ear drum movement, and failure of pressure equalization reduces auditory acuity by inhibiting ear drum and ossicular motion.

The most important function of the middle ear is to amplify and deliver sound vibrations from the ear drum to the inner ear, and the second most important function is to protect the inner ear from very loud sounds and physical trauma. Lever action of the ossicles appears to produce greater forces at the oval window than developed at the ear drum, and significant sound amplification occurs. When the ossicular chain is disrupted as by traumatic injury, infection, disease or the like, the reduction in transmitted pressure results in the loss of hearing.

Successful ossicular chain repair and/or reconstruction remains a major challenge for the practicing otologic surgeon. As will herein be described, a variety of prior art prosthetic devices have previously been proposed for replacement of various of the middle ear sound conducting ossicles. Suitable prosthetic devices may be comprised of a variety materials which have been suggested in the literature, some involving the use of autologous and homologous tragal cartilage, plastic materials such as polytetrafluoroethylene (TEFLON), and other plastic materials sold under the trade names Proplast and Plasti-Pore. Other prior art developments have encouraged the use of various inert metallic materials such as platinum, stainless steel and the like. However, a recent histological evaluation of tissue response to plastic materials appears to demonstrate adverse responses.

A recent experiment has revealed that the use of the aforedescribed plastic materials may result in the development of unwanted mucosa within the tympanic cavity, and multinucleated giant cells and macrophages may predominate in the porosity of plastic implants. For a detailed explanation of the foregoing, reference is directed to an article entitled *Tissue Response to Plastipore and Proplast Otologic Implants in the Middle Ears of Cats,* published in the American Journal of Otology, Volume 5, October 1983.

It would thus appear then that the use of neutral or chemically and physiologically inert metallic substances is physiologically advantageous. Moreover, notwithstanding the prior art developments in prosthetic devices, it is desirable to provide a system for total middle ear ossicular replacement.

A variety of prior art patents exist which are directed to prosthetic devices for partial middle ear ossicular replacement. For example U.S. Pat. No. 4,281,419 depicts a ball and socket structure from which a rigid, outwardly extending metallic shaft originates. The latter reference contemplates the surgical dimensioning of the shaft portion and termination of it with biocompatible material in contact with at least a portion of the existing middle ear ossicles.

U.S. Pats. No. 4,473,909 and 4,287,616 disclose auditory ossicular prosthetic devices essentially comprising a flat, plate-like end from which an elongated, generally rigid shaft projects. In both of the latter references the shaft is adapted to be fitted to the remaining ossicular structure of the damaged ear, requiring time consuming precision surgical adjustments and handling by the otologic surgeon.

Another prosthesis for partial ossicular replacement is illustrated in U.S. Pat. No. 3,196,462. The stapedial prosthesis therein disclosed in useful where only the stapes has sustained damaged. The latter reference discloses a generally tubular, barrel-like base adapted to be secured by the surgeon and an elongated rigid stem which extends towards a fat graft adapted to be employed in contact with the oval window.

U.S. Pat. No. 4,215,438 discloses a rigid, generally goblet-shaped prosthetic member preferably formed of stainless steel. The latter device includes a cup portion adapted to receive the capitulum of the stapes, and an integral stem portion which is adapted to be received through a hole drilled into the body of the incus. Another prosthetic device shown in U.S. Pat. No. 4,130,905 includes structure for attachment to the bridge of the human ear and an inwardly projecting stem adapted to contact the stapes.

Russian Pat. No. 584,860 discloses a convex plate terminating in an elongated, elastic tube adapted to be coupled to a portion of the existing ossicles. Russian Pat. No. 619,812 discloses an anvil ossicle prosthesis made from a titanium plate including two parallel leg pieces fixed together by an integral, perpendicular cross piece. The latter device ostensibly increases the effectiveness of sound transmissions through the middle ear. Russian Pat. No. 787,021 discloses an artificial ear bone prosthetic device comprised of plastic material including a generally cross-shaped head from which a slotted shaft projects. A cylindrical sleeve is positioned at a desired portion of the shaft to adapt the prosthetic device for the middle ear of the patient.

SUMMARY OF THE INVENTION

The present invention comprises an ossicular prosthesis for the total replacement of the ossicles of the middle ear. Preferably the apparatus is comprised of stainless steel, titanium, platinum or the like, and it includes two cooperating working sections which are adapted to extend completely across the middle ear for total replacement of the malleus, incus and stapes. In each of the embodiments of the present invention a separate tympanic membrane assembly cooperates with an oval window assembly, and the assemblies are axially, extensibly coupled together by cooperating, interfitting shaft structures.

In the best mode known to me a first assembly comprises an anchor structure adapted to be surgically coupled to the oval window. This anchor structure preferably includes a flange-like portion facilitating attachment to the oval window, and a socket which matingly receives the ball end of an outwardly extending, generally tubular shaft portion. Similarly, a second assembly includes a flanged base adapted to be coupled to the central portion of the reconstructed tympanic membrane. This flanged base includes a plurality of apertures to aid in suturing, and an integral base socket for receiving the terminal ball end of an inwardly projecting cylindrical shaft. Both of the aforementioned rigid shaft portions are thus mechanically anchored through ball and socket couplings which facilitate relative pivotal movement of the shaft structures to at least partially compensate for pressure differentials, vibration and other physical disturbances which may normally be encountered by the patient, thereby protecting against pressure necrosis at disc edges and preventing extrusion.

In the best mode of the invention the oval window assembly shaft is tubular, and it coaxially receives the reduced diameter cylindrical shaft of the tympanic membrane assembly to couple the two shafts in extensible, telescoping relation in which the two constituent assemblies are bridged together across the middle ear. However the teachings of the present invention also contemplate the possible use of a tubular shaft in the tympanic membrane assembly and a cooperating cylindrical shaft in conjunction with the oval window assembly. In either of the last mentioned cases when the two assembly shaft structures are thus coaxially coupled together, relative axial displacements are allowed, and thus, importantly, normal variations in air pressure experienced by the tympanic membrane may produce resultant self-compensating axial adjustment of the prosthesis. If, for example, the patient were to experience a loss in air pressure (i.e. perhaps on an airplane flight) the structural bridge between the oval window and the tympanic membrane will automatically expand, as relative axial outward movement of one of the shafts relative to the other is facilitated against limited frictional contact between the two portions.

In an alternative embodiment of the invention the oval window assembly comprises an elongated, twin member shaft which includes an integral, loop-like base adapted to be pivotally secured to the oval window. The tympanic membrane assembly is similar in structure. It preferably includes a shaft comprising a pair of closely spaced, parallel shaft members which emanate from and are integral with a loop-like base. The latter base is adapted to be pivotally secured to a plate member preferably disposed upon an interposed cartilage disk, and both the plate and the disk are sutured to at least a portion of the reconstructed tympanic membrane, near its center. The individual members of the oval window shaft occupy a first plane, and the similar individual members of the tympanic membrane shaft occupy a second plane. The first plane is perpendicular to the second, such that the oval window shaft may be axially, slidably coupled to the tympanic membrane shaft, thereby forming a mechanical bridge between the oval window and the tympanic membrane, capable of axial length adjustment in situ.

The present invention also contemplates the combination of ball-and-socket joints secured to the oval window and/or tympanic membrane which are linked together with a pair of twin member shafts of the type described above. Moreover, it is contemplated to optionally provide loop-like base portions pivotally coupled to both the oval window and the tympanic membrane which are joined together by telescoping coupled coaxially disposed shaft members.

Hence all embodiments of the present prosthesis provide a vehicle for total ossicular replacement, which vehicle inherently compensates for normal physical movement and disturbances experienced by the human ear, and in particular compensates for middle ear and atmospheric pressure variations normally encountered in day to day existence.

Thus a fundamental objective of the present invention is to provide a self-adjusting auditory ossicular prosthesis for the total reconstruction of the middle ear.

A similar fundamental objective is to provide an ossicular prosthesis which facilitates otological reconstruction and repair of traumatic ossicular damage.

A similar objective of the present invention is to provide an ossicular prosthesis which inherently and painlessly distributes middle ear forces. A relatively common disadvantage of know prior art prosthetic devices is that one end of conventional prosthetic shafts may begin extrusion by pressure necrosis of the tympanic membrane in response to air pressure variations, for example, deleteriously affecting hearing and causing failure of the reconstruction.

A similar objective is to provide a prosthesis of the character described which totally bridges the middle ear and operationally extends between and acoustically joins the tympanic membrane and the oval window with as little energy loss as structurally possible.

A similar objective of the present invention is to provide an ossicular prosthesis of the character described characterized by low inertial mass and excellent sound transmission characteristics.

Yet another objective of the present invention is to provide an ossicular prosthesis of the character described which reduces tissue rejection through choice of inert materials and physical self-alignment and self-adjustment of length.

A still further basic objective of the present prosthesis is to provide a vehicle for total ossicular replacement which reduces patient pain.

A fundamental objective is to provide a total ossicular replacement prosthesis for automatically adapting to normal air pressure differences and dimensional changes of the middle ear.

Another basic objective of the present invention is to reduce the tendency of ossicular prosthetic devices to extrude through the tympanic membrane.

A fundamental objective of the present invention is to avoid foreign body reactions typified by prior art "plastic" devices which may stimulate the development of macrophages and giant cells.

A still further objective of the present invention is to provide a prosthesis for total ossicular replacement of the character described, which prosthesis is not prone to development of inflammatory infiltrates which may alter its long-term function.

Yet another objective of the present invention is to minimize foreign body phagocytic responses following middle ear reconstructive surgery.

Another fundamental objective of the present invention is to provide a remedy for long standing pyogenic infection of the middle ear, enabling reconstruction of a functional middle ear in the once infected suppurative middle ear.

An important and basic objective of the present invention is to provide an ossicular prosthesis which inherently seeks to align and orient itself in a proper operative position and adjust its length to changing dimensions of the middle ear.

A basic objective of the present invention is to provide a total ossicular prosthesis which moves in direct relation to atmospheric pressure changes while maintaining a continuous and substantially painless functional acoustical bridge within the middle ear between the tympanic membrane and the oval window.

These and other objectives and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 4 is an enlarged, fragmentary isometric view of the tympanic membrane assembly of the best mode of the invention;

FIG. 5 is an enlarged, fragmentary isometric view showing the oval window assembly of the best mode of the present prosthesis;

FIG. 6 is an enlarged, fragmentary, isometric view illustration a portion of the telescopingly coupled shaft assemblies of the best mode;

FIG. 7 is a sectional view taken generally along line 7-7 of FIG. 6;

FIG. 9 is a fragmentary, exploded, isometric view illustrating an alternative mode of the present invention;

FIG. 10 is an enlarged fragmentary, isometric view of the tympanic membrane assembly of the alternative embodiment of the prosthesis illustrated in FIG. 9;

FIG. 11 is an enlarged, fragmentary, isometric view of the oval window assembly of the alternative embodiment of the present invention illustrated in FIG. 9;

FIG. 12 is an enlarged, fragmentary, isometric view of the coupled shaft portions of the cooperating tympanic membrane and oval window assemblies of the alternative mode of the present invention illustrated in FIG. 9;

FIG. 13 is an enlarged, fragmentary sectional view taken generally along line 13—13 of FIG. 12;

FIG. 14 is a fragmentary, isometric view of the alternative embodiment of FIGS. 9-13;

DETAILED DESCRIPTION OF THE DRAWINGS

Figure 1:
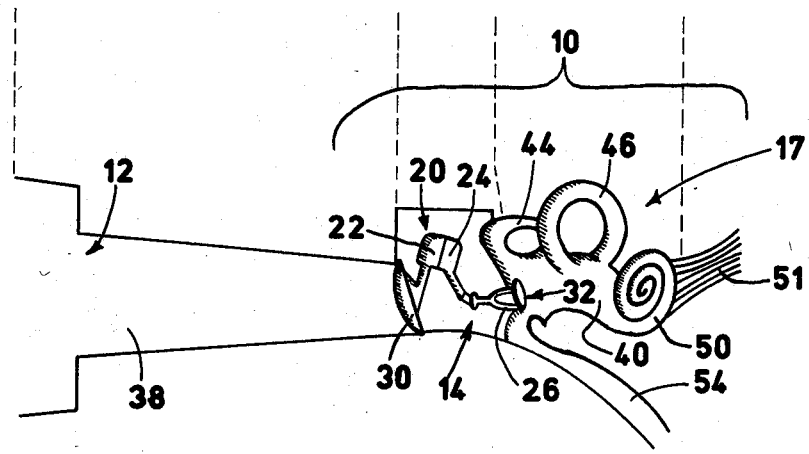
FIG. 1 is a fragmentary, diagrammatic pictorial view illustrating portions of the typical human outer, middle and inner ear.

With initial reference now to FIG. 1 of the appended drawings, the well known structure of the human ear has been generally designated by the reference numeral 10. As will be appreciated by those skilled in the relevant medical arts, the human ear includes outer ear structure 12, a middle ear section 14, and an inner ear section 17. Designated generally by the reference numeral 20 are the auditory ossicles comprising a malleus 22 joined to an incus 24 and a stapes 26 which extend between the tympanic membrane 30 (forming the edge of the external ear 12) and the fenestra vestibuli (oval window) generally designated by the reference numeral 32. Sounds trasmitted to the tympanic membrane 30 through the ear canal 38 are physically transmitted through the middle ear 14 into contact with the bony labyrinth 40 via the aforementioned middle ear ossicles, the malleus, incus and stapes. The inner ear 17 also includes a lateral semicircular canal 44, a posterior semicircular canal (not shown), and a superior semicircular canal 46, the cochlea 50, and a plurality of auditory nerve fibers 51. Air flow communication between the middle ear 14 and the nasopharynx is facilitated by the Eustachian tube 54. As mentioned earlier, although traumatic shock can damage the ossicles 20 of the middle ear 14, one common source of chronic disease necessitating complete middle ear ossicular replacement is necrotizing ascending infection through the Eustachian tube 54 into the interior of the middle ear.

All of the embodiments of the present invention contemplate virtually total replacement of the inner ear ossicles 20. Thus each embodiment of the present invention is adapted to replace the stapes 26, the incus 24 and the malleus 22 of the human middle ear 14.

Figure 2:
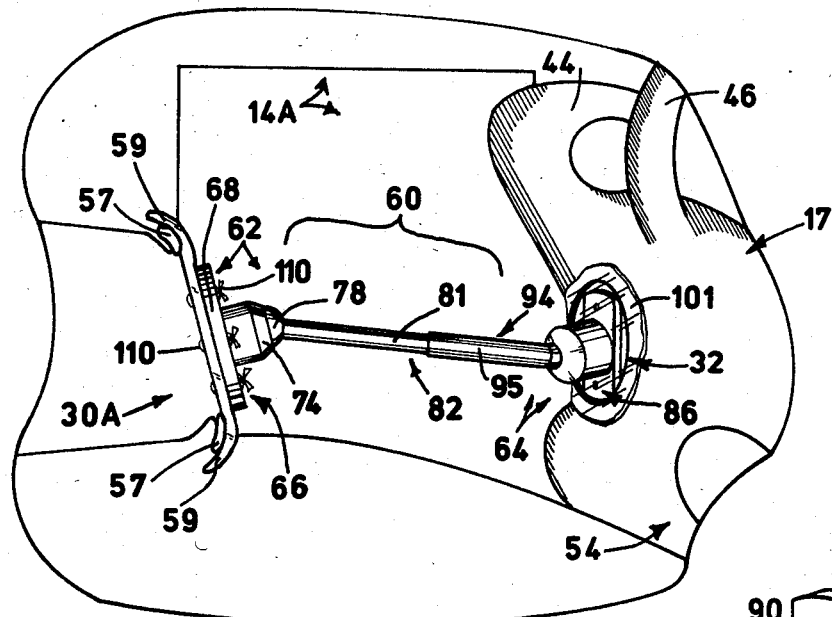
FIG. 2 is an enlarged, fragmentary view illustrating a substantially surgically reconstructed middle ear in which a prosthesis constructed in accordance with the best mode of the present invention has been implanted.
Figure 3:
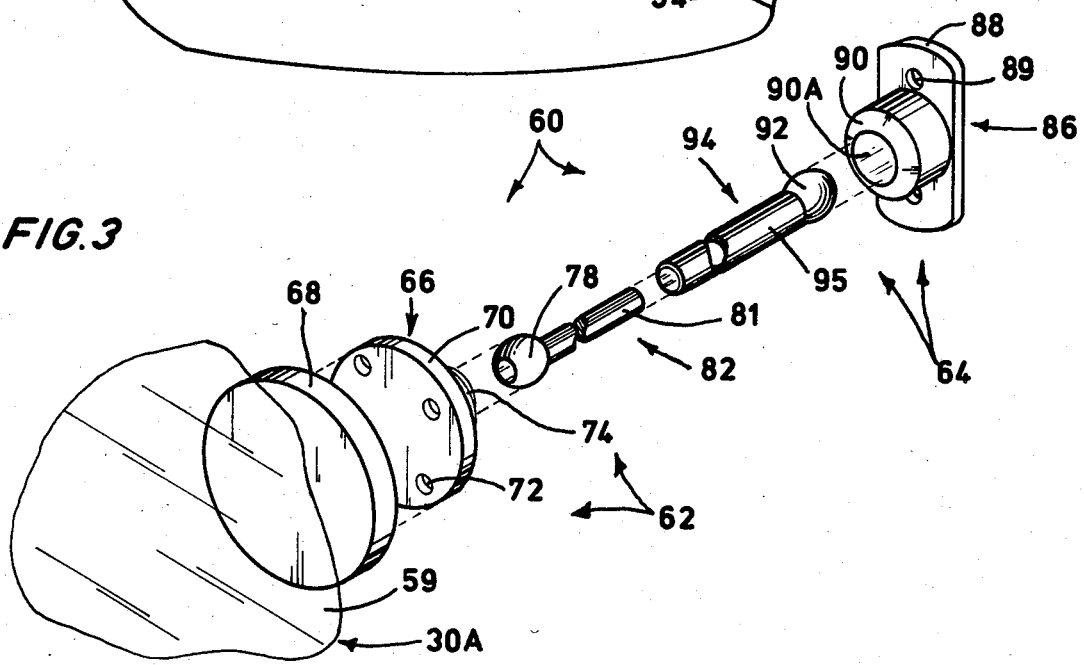
FIG. 3 is an enlarged, fragmentary, exploded isometric view of the preferred prosthesis.

With additional reference now directed to FIGS. 2-8, the best mode of the present invention is generally designated by the reference numeral 60. Preferably prosthesis 60 comprises a pair of cooperating assemblies generally designated by the reference numerals 62 and 64. Portion 62 (i.e. the tympanic membrane assembly) is adapted to be coupled to at least a portion of the tympanic membrane, and it includes an anchor member generally designated by the reference numeral 66 which, as explained hereinafter, is adapted to be sutured to at least a portion of the reconstructed tympanic membrane 30A (FIGS. 2,3) near its center with the aid of a surgically interposed cartilage disc 68. As best illustrated in FIGS. 2-4, and as will hereinafter be described in detail, the present invention contemplates that the tympanic membrane usually must be surgically reconstructed. In FIG. 2, for example, remaining remnants of the original tympanic membrane have been designated by the reference numeral 57. Prior to installation of any of the prostheses of the present invention the damaged tympanic membrane will be replaced with a sheet-like portion of fascia (i.e. such as fascia 59) yielding a reconstructed tympanic membrane. Proper candidate fascia may be surgically obtained from the temporalis muscle area above the ear. The tympanic membrane assembly of all modes of the present invention is then sutured to this reconstructed membrane.

The anchor means 66 preferably comprises a generally circular base 70 including a plurality of apertures 72 (FIG. 3) and a generally tubular socket portion 74 which is integral with base 70 and projects upwardly, concentrically therefrom. The socket orifice 76A (FIG. 8) is adapted to receive the ball portion 78 of a preferably metallic, shaft assembly 82. Assembly 82 includes a rigid, elongated, cylindrical shaft member 81 adapted to project away from the tympanic membrane assembly 62 towards the oval window assembly 64. The ball and socket configuration facilitated by ball 78 received within socket orifice 76A permits a swivelling motion of shaft 81 relative to the tympanic membrane.

The oval window assembly 64 is somewhat similar to the previously described tympanic membrane assembly. It comprises a flanged anchor assembly generally designated by the reference numeral 86 which is adapted to be coupled surgically to the oval window 32. Assembly 86 includes a generally rectangular base 88 which contacts the stapes footplate and includes apertures 89 for facilitating surgical implantation. A generally tubular, integral socket portion 90 extends outwardly away from base 88, and it is adapted to receive and capture the ball end 92 of shaft assembly 94. Ball 92 is attached to the elongated, tubular shaft 95 which extends toward the tympanic membrane assembly 62. Ball 92 is operationally coupled within the aperture socket 90A (FIG. 8) and it will be apparent that shaft 95 is thus adapted to be swivelled with respect to the oval window whereby orientation and positional compensation of the prosthesis 60 is facilitated.

Figure 8:
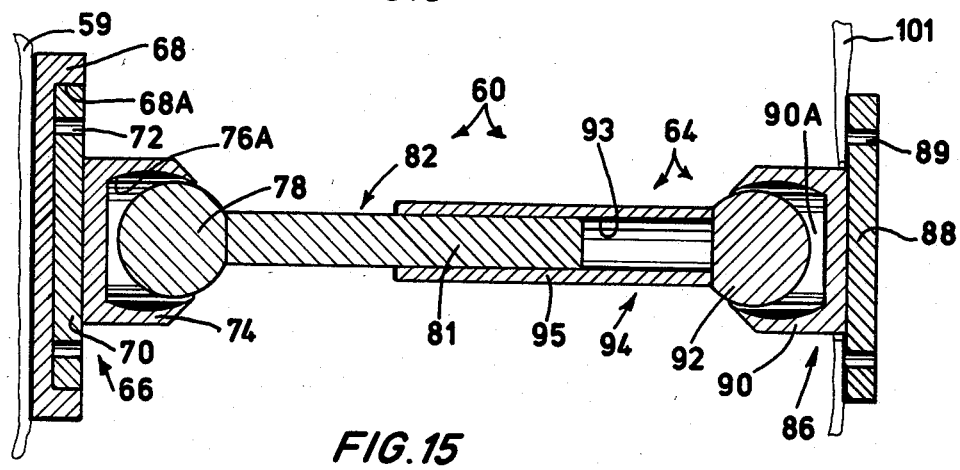
FIG. 8 is an enlarged, longitudinal, fragmentary sectional view illustrating the preferred prosthesis.

Importantly, and as will best be appreciated from an inspection of FIGS. 2, 3 and 8, shafts 81 and 95 are telescopingly fitted together. In other words, shaft 81 is slidably coaxially received within interior 93 of the tubular shaft 95 such that limited relative axial displacement between the coupled shaft members (against minimal predetermined friction) is facilitated. Hence the effective mechanical operative acoustic path provided between the inner and outer ears by the ossicular prosthesis 60 may be varied in length.

This extremely important feature of extensibility prevents extrusion of one or more portions of the apparatus through the tympanic membrane or oval window in response, for example, to the exposure of the patient to extremely varying pressure situations. Further, as evidenced, for example in FIG. 2, the concurrent swivelling action of the cooperating pair of ball and socket assemblies along with axial shaft displacements facilitates the assumption of a variety of inner configurations somewhat equivalent to the natural variance in geometry assumed by the middle ear ossicles 22, 24, 26 previously described.

Surgical implantation of the prosthesis 60 is facilitated by first entering the ear through an incision formed in the posterior part of the ear canal approximately 4 to 6 millimeters from the ear drum 30. Subsequent exploration of the middle ear by the otological surgeon will thence determine the state of the ossicles 20. Where there is sufficient ossicular residue to reconstruct the ear with the patients' own ossicles, then reconstruction rather than replacement would be effectuated. There are a number of prior art prostheses for correcting partial ossicular damage. Stapedial prostheses, for example, are known in the prior art. In other words, for the use of known prior art devices at least a portion of the operative middle ear ossicles are required. Where ossicular residue includes a mobile foot plate (i.e. an operative base portion of the stapes), and malleus-incus unit, the use of a stapedial prosthesis may be effective.

It is often the case especially in chronic suppurative otitis media in response to a long standing pyogenic infection in the middle ear that most of the ossicles are damaged beyond repair. Such a condition is not usually the result of violent physical contact which, for example may produce well known sports-related injuries. Instead, one of the most important necessitating factors for use of the total prosthesis 60 may be caused by an ascending infection from the nose through the previously mentioned Eustachian tube 54.

Thus the surgeon must first assess and evaluate the condition of all the middle ear ossicles and then one of several surgical choices would be mandated. A typical stapedial prosthesis for replacement of the stapes may be employed. Also, partial ossicular replacement may be effectuated by homographed ossicles. Sometimes autogenous material from other portions of the patients' body may be employed for ossicular reconstruction. If ossicular reconstruction is impractical, or partial ossicular replacement with a conventional prosthesis is not appropriate, then total ossicular repair is mandated, and the prosthesis 60, is surgically implanted through an essentially two step process.

The first stage of implantation is to prepare the reception site at the oval window, usually necessitating partial removal of mucosa covering the periphery of the oval window. Essentially a straight pic or hoe is employed to incise the mucosa covering the oval window and strip it off circumferentially. Alternatively laser surgery may be employed to remove the mucosa. Incision of the mucosa naturally results in bleeding. Hence, in order to control bleeding, it is desirable to employ a pledget of cotton treated with some adrenaline on it as well as local anesthetic. A piece of fascia 101 (FIG. 5) is removed from the temporalis muscle and is fashioned to surround the base 88 of the anchor means 86. This smaller flange portion comprises a "footplate" and it is then secured to the fascia, covering the oval window, with additional pledgets of Gelfoam. It is important that the latter prosthesis base be properly centered on the mobile footplate and properly oriented with its long axis parallel to the long axis of the footplate. Once aligned in this fashion, the Gelfoam pledget is packed down on it to provide minimal pressure facilitating permanent adherence to the oval window. Post surgical healing with fibrous connective tissue unites the base 88, the mobile footplate 103, and the fascia portion 101.

The second stage of the preferred surgical implantation procedure is the preparing of the tympanic membrane remnant. In some cases an intact tympanic membrane would be encountered, but in most instances there would be but a disc or rim of tympanic membrane with a large perforation. For purposes of this discussion, it is assumed that the only remnants 57 (FIG. 2) remain. At this point reconstruction of the tympanic membrane would take place by using homologous or autologous tissue. Reconstructive fascia 59 (FIGS. 2, 3) may be surgically installed relative to the annulus tympanicus 112 (FIG. 4).

The cartilage disc 68 is employed to properly distribute forces developed upon and about the reconstructed tympanic membrane. The tympanic portion of the prosthesis (i.e. base 70) would be positioned near the center of the tympanic membrane. The interposed cartilage disc 68 is then cut with a punch to create a buffer to insert between the tympanic membrane and the tympanic portion (i.e. base 70) of the prosthesis. Candidate autologous cartilage may be obtained from the Tragus of the ear; homologous cartilage can also be obtained from a cartilage storage bank. The tympanic membrane assembly is then sutured into place by passing regular surgical Dexon sutures 110 through aperture 72 and base 70, through the fascia 59, and through the cartilage disk 68. The basic advantage of the cartilage disk 68 is in preventing direct contact between the rigid stainless steel base with the reconstructed tympanic membrane. Further, force distribution upon the reconstructed ear drum 30A by the cartilage disk 68 prevents pressure necrosis or stress-induced extrusion.

Finally, the stem-like shaft portions of each assembly 62 and 64 are joined together. The lesser diameter cylinder 81 is telescoped into tubular shaft member 95 by surgically pressing down within interior 93 to a length suitable for the circumstances of the patient. The telescoping feature of the combined shafts 81, 95 permit length compensations between the reconstructed ear drum and oval window.

With reference now directed to FIGS. 9-15, an alternative length-compensating prosthesis is generally designated by the reference numeral 200. As in the case of the previously described prosthesis, prosthesis 200 is adapted to be surgically implanted within a middle ear 14B (FIG. 14) wherein it extends between the reconstructed tympanic membrane 202 and the reconstructed oval window 204 area of the ear.

The oval window assembly 208 comprises elongated shaft means generally designated by the reference numeral 210, which includes an integral base portion 212 adapted to be secured to the oval window. Shaft portion 210 includes a pair of elongated, rigid, preferably metallic and closely spaced apart shaft members 214, 216 which are integrally joined together in the generally rectangular loop 218 forming base 212. Preferably loop 218 is secured to the mobile footplate 222 in the oval window by fascia 224, which is drawn through the loop 218 and across the oval window area. The substantially parallel shaft members 214, 216 extend outwardly from the oval window towards the outer ear (but within the middle ear area) and towards the cooperating, spaced apart tympanic membrane assembly 201.

The tympanic membrane assembly 201 includes elongated shaft means generally designated by the reference numeral 232 having an integral base portion generally designated by the reference numeral 234. The shaft means 232 actually includes a pair of elongated, closely spaced apart, and parallel members 238, 239 which originate from the loop 242 forming the base 234. Loop 242 is adapted to be pivotally secured by a plurality of tabs 250, which emanate from and are integral with a thin, generally circular metallic base plate 262. Preferably the base plate is secured within a cartilage disk 264 which is sutured to the reconstructed tympanic membrane 271 comprised of fascia which has been surgically installed as in the previous discussion. The tympanic membrane assembly shaft 232 extends towards the inner ear and is adapted to be to axially coupled to shaft member 210 of the previously described oval window assembly.

Figure 15:
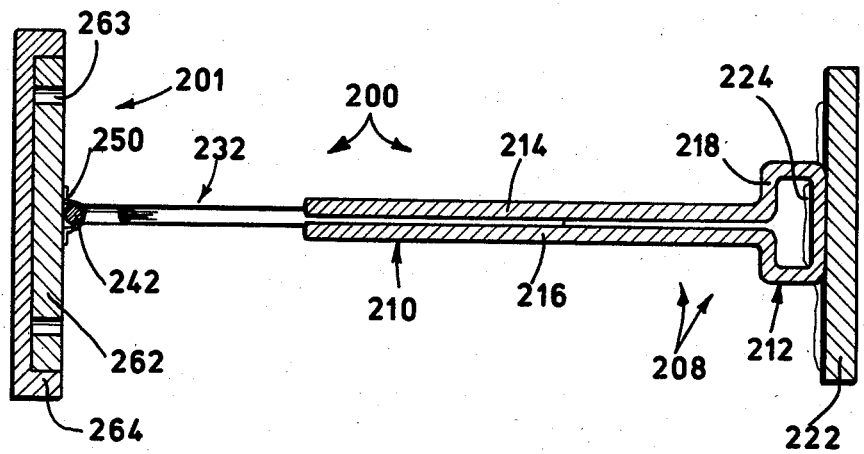
FIG. 15 is an enlarged, fragmentary, longitudinal sectional view of the alternative embodiment of FIGS. 9-14.

Importantly, the loop portion 218 is permitted to pivot relative to the mobile footplate 222 by the effects of the fascia 224. Similarly, the loop 242 of the tympanic membrane assembly 201 pivots with respect to the metallic base 262 because of the mounting tabs 250. As best illustrated in FIGS. 10 and 15, the cartilage disk and the base plate 262 are sutured to the reconstructed fascia 271. The suture knots 277 are tied to secure the plate 262 to the cartilage disk 264 and the fascia 271. Several apertures 263 are defined in plate 262 to permit ready suturing.

With reference now directed to FIGS. 12 and 13, it will be apparent that shaft assemblies 232 and 210 are adapted to be axially coupled together. As viewed in FIG. 13, the closely parallel individual shaft portions of each shaft assembly are oriented generally at the vertices of a square and clearance space between the four parallel members is generally designated by the reference numeral 253. Thus, each pair of shaft members generally occupy a plane, and said planes are orthogonal to one another. In other words, the generally elongated concave space formed on opposite sides of the parallel shaft members is occupied by the shaft members of the cooperating assembly. In such a fashion the oval window assembly and the tympanic membrane assembly of prosthesis 200 are extensibly axially coupled together. Thus the effective bridge between the tympanic membrane and the oval window of the patient may adjust itself in length to compensate for pressure differentials as previously described. In combination with the previously described pivotal mounting of the corresponding base loop portions, prosthesis 200 may assume a variety of angular and extensible orientations inherently providing positional compensation.

Figure 16:
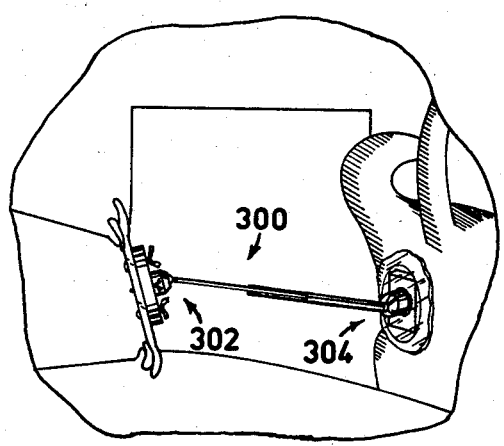
FIG. 16 is a fragmentary pictorial view of a third embodiment of the present invention; and, FIG. 17 is a fragmentary pictorial view of a fourth embodiment of the present invention.

In FIG. 16 a third embodiment has been generally designated by the reference numeral 300. The tympanic membrane assembly 302 is similarly extensibly axially coupled to an oval window assembly 304 to form a bridge across the middle ear. However, assembly 302 includes a ball and socket tympanic membrane anchor as in the case of embodiment 60, joined with an extensible shaft similar to the shaft means 210, 232 described in conjunction with embodiment 200.

Figure 17:
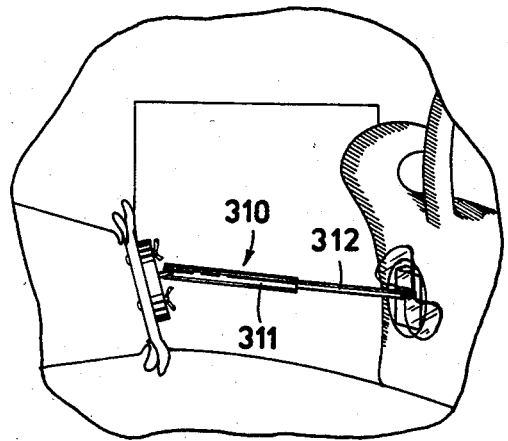

FIG. 17 reveals a fourth embodiment generally designated by the reference numeral 310, wherein telescopingly extensible shaft means 311 and 312 are employed as in the case of previously described embodiment 60. However, mode 310 contemplates that the telescoped shaft members bridging through the middle ear terminate in loop-like bases similar to loops 218, 242 previously described in conjunction with embodiment 200.

From the foregoing, it will be seen that this invention is one well adapted to obtain all the ends and objectives herein set forth, together with other advantages which are obvious and which are inherent to the structure.

It will be understood that certain features and subcombinations are of utility and may be employed without reference to other features and subcombinations. this is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A surgically implantable, length compensating auditory ossicular prosthesis for reconstruction of the ossicles of the middle ear, said prosthesis comprising:
an oval window assembly comprising:
elongated shaft means having a base portion adapted to be surgically coupled to to the oval window in pivotal relation therewith, and an integral, cooperating shaft portion extending outwardly from said base portion away from said oval window, said shaft portion comprising a pair of elongated, closely spaced, substantially parallel shaft members, each of said shaft members being integrally joined together in loop means forming said base portion, said loop means adapted to be sutured to at least a portion of said oval window permitting limited pivoting between said last mentioned shaft means and said oval window; and,
a cooperating tympanic membrane assembly comprising:
elongated shaft means having a base portion adapted to be surgically coupled to at least a portion of the reconstructed or original tympanic membrane in pivotal relation therewith, and a cooperating shaft portion extending outwardly from said base portion away from said tympanic membrane; said last mentioned shaft portion comprising a pair of elongated, closely spaced, substantially parallel shaft members, each of said last mentioned shaft members being integrally joined together in loop means forming said base portion of said last mentioned shaft means, said loop means adapted to be secured to at least a portion of said tympanic membrane permitting limited pivoting between said last mentioned shaft means and said tympanic membrane;
wherein said shaft portion of said oval window assembly is adapted to be frictionally, axially coupled to said shaft portion of said tympanic membrane assembly whereby to provide an axially extensible bridge between said oval window and said tympanic membrane capable of varying in length to accomodate variations in spacing between the oval window and the tympanic membrane with changes of air pressure.

2. The prosthesis as defined in claim 1 wherein:
the shaft members of said shaft means of said oval window assembly occupy a first plane;
the shaft members of said shaft means of said tympanic membrane assembly occupy a second plane; and,
said first plane is substantially orthogonal with respect to said second plane, whereby said oval window shaft means may be axially, slidably coupled to said tympanic membrane shaft means.

3. A surgically implantable, length compensating, auditory ossicular prosthesis for reconstruction of the ossicles of the middle ear, said prosthesis comprising:
an oval window assembly comprising elongated shaft means having a base portion adapted to be surgically coupled to the oval window in pivotal relation therewith, and a cooperating shaft portion extending outwardly from said base portion away from said oval window, wherein the shaft means associated with said oval window assembly comprises a pair of elongated, closely spaced, substantially parallel shaft members, each of said shaft members being integrally joined together in loop means forming said base portion of said last mentioned shaft means, said loop means adapted to be sutured to at least a portion of said oval window permitting limited pivoting between said last mentioned shaft means and said oval window;
a cooperating tympanic membrane assembly comprising elongated shaft means having a base portion adapted to be surgically coupled to at least a portion of the reconstructed or original tympanic membrane in pivotal relation therewith, and a cooperating shaft portion extending inwardly from said base portion away from said tympanic membrane; wherein the shaft means associated with said tympanic membrane assembly comprises a pair of elongated, closely spaced, substantially parallel shaft members, each of said last mentioned shaft members being integrally joined together in loop means forming said base portion, said loop means adapted to permit limited pivoting between said last mentioned shaft means and said tympanic membrane; and,
wherein said shaft portion of said oval window assembly is adapted to be frictionally, axially coupled to said shaft portion of said tympanic membrane assembly whereby to provide an axially extensible bridge between said oval window and said tympanic membrane capable of varying in length to accomodate variations in spacing between the oval window and the tympanic membrane.

4. The prosthesis as defined in claim 3 wherein:
the shaft members of said shaft means of said oval window assembly occupy a first plane;
the shaft members of said shaft means of said tympanic membrane assembly occupy a second plane; and,
said first plane is substantially orthogonal with respect to said second plane, whereby said oval window shaft means may be axially, slidably coupled to said tympanic membrane shaft means.

5. A surgically implantable, length compensating auditory ossicular prosthesis for reconstruction of the ossicles of the middle ear, said prosthesis comprising:
an oval window assembly comprising elongated shaft means having a base portion adapted to be surgically coupled to the oval window in pivotal relation therewith; a cooperating shaft portion extending outwardly from said base portion away from said oval window; and, first flanged anchor means adapted to be surgically coupled to the oval window;
wherein said first flanged anchor means includes integral socket means and a plurality of apertures for facilitating subsequent tissue ingrowth, and said base portion of said oval window means shaft means terminates in first ball means adapted to be coupled to said socket means to permit limited swiveling of said last mentioned shaft means with respect to said last mentioned anchor means;
a cooperating tympanic membrane assembly comprising elongated shaft means having a base portion adapted to be surgically coupled to at least a portion of the reconstructed or original tympanic membrane in pivotal relation therewith; a cooperating shaft portion extending inwardly from said base portion away from said tympanic membrane; and second flanged anchor means adapted to be surgically secured to at least a portion of the tympanic membrane, said last mentioned flanged anchor means including integral socket means and a plurality of apertures for facilitating subsequent tissue ingrowth; wherein said tympanic membrane assembly shaft means base portion terminates in second ball means adapted to be coupled to said last mentioned socket means whereby to permit relative swiveling of said last mentioned shaft means with respect to said last mentioned anchor means; and, one of said shaft means of said tympanic membrane and oval window assemblies being tubular and the other one of said shaft means being generally cylindrical, wherein said shaft means of said tympanic membrane assembly may be telescopingly coupled to said shaft means of said oval window assembly whereby to provide an axially extensible bridge between said oval window and said tympanic membrane capable of varying in length to accomodate variations in spacing between the oval window and the tympanic membrane.

6. The prosthesis as defined in claim 5 wherein the shaft means of said tympanic membrane assembly is cylindrical and the shaft means of said oval window assembly is tubular and of a larger diameter whereby, after implantation of the two assemblies, they may be easily fitted together by centering the tympanic membrane assembly shaft relative to the exposed oval window assembly tubular shaft and thereafter frictionally forcing them together.

* * * * *